United States Patent
Haimerl et al.

(10) Patent No.: US 9,370,317 B2
(45) Date of Patent: Jun. 21, 2016

(54) DETERMINING A PLANE OF ANATOMICAL BODY PART

(75) Inventors: Martin Haimerl, Gilching (DE); Mario Schubert, Poing (DE); Sabine Kling, Taufkirchen (DE)

(73) Assignee: Brainlab AG, Feldkirchen (DE)

( * ) Notice: Subject to any disclaimer, the term of this patent is extended or adjusted under 35 U.S.C. 154(b) by 0 days.

(21) Appl. No.: 13/394,612

(22) PCT Filed: Sep. 8, 2009

(86) PCT No.: PCT/EP2009/061623
§ 371 (c)(1),
(2), (4) Date: May 17, 2012

(87) PCT Pub. No.: WO2011/029466
PCT Pub. Date: Mar. 17, 2011

(65) Prior Publication Data
US 2012/0316469 A1    Dec. 13, 2012

(51) Int. Cl.
*A61B 5/103* (2006.01)
*A61B 5/00* (2006.01)

(52) U.S. Cl.
CPC ............... *A61B 5/103* (2013.01); *A61B 5/4528* (2013.01); *A61B 5/6878* (2013.01)

(58) Field of Classification Search
CPC ..... A61B 5/4528; A61B 5/103; A61B 5/0053
USPC ................................................. 600/587, 595
See application file for complete search history.

(56) References Cited

U.S. PATENT DOCUMENTS

2008/0132783 A1    6/2008    Revie et al.
2009/0101158 A1*   4/2009    Kozak et al. .................. 128/898

FOREIGN PATENT DOCUMENTS

EP    1 611 863 A1    1/2006
EP    1 894 538 A1    3/2008
(Continued)

OTHER PUBLICATIONS

International Search Report for International Application No. PCT/EP2009/061623 dated May 27, 2010.
(Continued)

*Primary Examiner* — Sean Dougherty
*Assistant Examiner* — Daniel Cerioni
(74) *Attorney, Agent, or Firm* — Tucker Ellis LLP

(57) ABSTRACT

A data processing method for determining the position of a main plane of an anatomical body part, comprising the steps of: • providing absolute auxiliary point data which describe the position of at least one actual auxiliary point of the body part relative to a marker device attacked to the body part, the at least one actual auxiliary point being outside the main plane; • providing relative point data which constrain the possible positions of the main plane relative to the at least one actual auxiliary point; • providing absolute main point data which describe the position of one or two actual main points of the body part relative to the marker device attached to the body part, said one or two actual main points lying in the main plane and/or calculating the position of at least one virtual main point relative to the marker device, said at least one virtual main point being in the main plane and being calculated based on the absolute auxiliary point data and the relative point data; • calculating a position of the main plane relative to the marker device, wherein the calculation uses the relative point data and auxiliary point data as well as the provided absolute main point data and/or the calculated position of the at least one virtual main point.

17 Claims, 2 Drawing Sheets

(56) References Cited

FOREIGN PATENT DOCUMENTS

| EP | 2 008 606 A1 | 12/2008 |
| EP | 2 051 096 A2 | 4/2009 |

OTHER PUBLICATIONS

Digioia et al., "Surgical navigation for total hip replacement with the use of hipnav", Operative Techniques in Orthopaedics, Saunders, Philadelphia, PA, Jan. 1, 2000, vol. 10, No. 1, pp. 3-8.

* cited by examiner

DETERMINING A PLANE OF ANATOMICAL BODY PART

This application is a national phase of International Application No. PCT/EP2009/061623 filed Sep. 8, 2009 and published in the English language.

The present invention relates to determining a plane of an anatomical body part (for example a pelvis or head) which shall be referred to in the following as a main plane. The "anatomical body part" shall also be referred simply as the "body part" for short, and the "anatomical pelvis" simply as the "pelvis". A main plane is in particular a plane which is used in surgery (for example in brain or hip surgery) as a reference for defining the positions of other anatomical structures or body parts (for example the acetabulum). A main plane is in particular a plane which can be defined by anatomical landmarks of the anatomical body part (for example the pelvis). Planes which can be defined by these landmarks and/or which are used for defining the position of the femur or acetabulum are in particular the mid-sagittal plane (MSP) or the anterior pelvic plane (APP).

Generally speaking, at least two planes of the anatomical body part (for example the pelvis) are defined in order to determine a coordinate system with respect to which the above-mentioned position of the acetabulum can be defined. One of these planes is the aforementioned main plane (for example the MSP), the other plane can be a plane referred to here as the auxiliary plane (for example the spinae joint center plane or SJCP to be defined later) or can be a plane referred to here as the standard plane (for example the APP). Like the main plane, the auxiliary plane, and standard plane are preferably defined by landmarks of the anatomical body part (for example the pelvis).

It is advantageous to determine the position of the main plane reliably and with a sufficient degree of accuracy to allow the position of the other anatomical structures or body parts (for example the acetabulum) to be determined with a sufficient degree of accuracy.

In accordance with a common prior-art method, the pelvis is registered in a supine position in particular for hip surgeries and then turned over to a lateral position. In the supine position, landmarks are detected by means of a pointer in order to determine the location of landmarks on the MSP and APP relative to a marker device fixed to the pelvis.

Reference is also made to US 2008/132783 A1. In accordance with this patent application, points are determined in three cardinal planes. Reference is also made to US 2003/0153829, US 2002/0077540 and WO 2005/084541.

The object of the invention is to allow a position, in particular an orientation of a main plane of an anatomical body part (for example a pelvis) to be determined on the basis of the position of (main and auxiliary) points which in particular represent landmarks. Preferably, all represented landmarks can be detected (scanned) when the patient is in one position, in particular the lateral position.

The above object is solved by the subject-matter of the independent claims. The dependent claims are directed to advantageous embodiments.

As far as herein the "position" of a plane is mentioned, the term position can mean absolute location of the plane or just orientation of the plane. In particular determination of the latter is often sufficient in hip surgery since the orientation of the plane relative to the orientation of the acetabulum is of main interest for the surgeon.

One advantage of the invention is that it is not necessary to reposition the anatomical body part (for example the pelvis) and thus the patient on the table. Furthermore, the present invention relies in particular on landmarks which are easily accessible for a surgeon. In particular, points which are symmetrical to the auxiliary points with respect to the main plane and remote from the main plane (for example the ASIS point) do not have to be detected. These symmetrical and/or remote points can be difficult to detect.

Advantageously, determining the main plane does not rely on fluoroscopic images produced during surgery. Thus, the exposure of the patient and operating theatre staff to radiation is reduced.

Advantageously, the present invention can rely on position data for landmarks which can be detected to a high degree of accuracy and which are in particular not covered by soft tissue or fat. These position data are in particular detected by means of a pointer (see below).

The method in accordance with the invention is in particular a data processing method. The data processing method is preferably performed using technical means, in particular a computer. The computer in particular comprises a processor and a memory in order to process the data, in particular electronically. The calculating steps described are in particular performed by a computer. Steps of determining or calculating are in particular steps of determining data within the framework of the technical data processing method, in particular within the framework of a program. A computer is in particular any kind of data processing device. A computer can be a device which is generally thought of as such, for example desktop PCs or notebooks or netbooks, etc., but a computer can be also any programmable apparatus, such as a mobile phone or an embedded processor. In particular, a computer can comprise a system (network) of "sub-computers", wherein each sub-computer represents a computer in its own right. A computer in particular comprises interfaces in order to receive data and/or to perform an analog-to-digital conversion.

Merely as a non-limiting example of an anatomical body part, the term "anatomical pelvis" or "pelvis" is used in the following instead of "anatomical body part".

The data processing method of the present invention is a method for determining the position, in particular orientation of the main plane of the anatomical pelvis. The pelvis is in particular the pelvis of a subject (patient) who is in particular lying in a lateral position. The position, in particular orientation of the main plane is in particular determined relative to a marker device which is attached to the pelvis.

A marker device can for instance be a reference star or a pointer or one or more (individual) markers in a predetermined spatial relationship. A marker device comprises one, two, three or more markers in a predetermined spatial relationship. This predetermined spatial relationship is in particular known to a navigation system, for example stored in a computer of the navigation system.

The function of a marker is to be detected by a marker detection device (for example, a camera or an ultrasound receiver), such that its spatial position (i.e. its spatial location and/or alignment) can be ascertained. The detection device is in particular part of a navigation system. The markers can be active markers. An active marker emits for example electromagnetic radiation and/or waves, wherein said radiation can be in the infrared, visible and/or ultraviolet spectral range. The marker can also however be passive, i.e. can for example reflect electromagnetic radiation from the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and may therefore be referred to as a marker sphere; markers can also, however, exhibit a cornered—for example, cubic—shape.

A "reference star" refers to a device which a number of markers, advantageously three markers, are attached to, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation method, in order to enable the corresponding reference star to be identified by a surgical navigation system on the basis of the position of the markers relative to each other. It is thus also then possible for the objects (for example, instruments and/or parts of a body) to which the reference star is attached to be identified and/or differentiated from each other. In a surgical navigation method, the reference star serves to attach a plurality of markers to an object (for example, a bone or a medical instrument) in order to be able to detect the position of the object (i.e. its spatial location and/or alignment). Such a reference star in particular comprises a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

The position of the main plane is in particular described in a coordinate system of a navigation system, in particular a surgical navigation system (also referred to as a computer-assisted navigation system or image-guided surgery system).

A navigation system, in particular a surgical navigation system, is understood to mean a system which may comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) comprises in particular a processor (CPU), a working memory, advantageously an indicating device for issuing an indication signal (for example, a visual indicating device such as a monitor and/or an audio indicating device such as a loudspeaker and/or tactile indicating device such as a vibrator) and advantageously a permanent data memory, wherein the data processing device processes navigation data forwarded to it by the receiver and can advantageously output guidance information to a user via the indicating device. The navigation data can be stored in the permanent data memory and for example compared with data which have been stored in said memory beforehand.

According to an embodiment of the invention, absolute main point data are provided. These absolute main point data can describe the position of one (actual) main point or the position of two (actual) main points of the pelvis relative to the marker device which is in particular attached to the pelvis or of more (actual) main points. In particular, the absolute main point data describe the position of only one main point of the pelvis or the position of only two main points of the pelvis relative to the marker device. The main points are points which lie in the main plane and the position of which is in particular defined by landmarks of the pelvis. Generally the main points can lie anywhere on the main plane. According to another embodiment, no absolute main point data are provided but instead virtual main points are calculated based on the absolute auxiliary point data and the relative point data.

The virtual main points lie in the main plane and can but have not to lie in the body part. These calculated virtual main points can be used for the further determination, in particular calculation in accordance with the described inventive method in the same way as the actual main points described by the absolute main pint data. According to a further embodiment both the provided actual main points and the calculated virtual main points are used for the further determination in accordance with the invention.

A landmark is a defined position of an anatomical characteristic of an anatomical body part which is always identical or recurs with a high degree of similarity in the same anatomical body part of multiple patients. Typical landmarks are for example the anterior superior iliac spine (ASIS) points or the tips of the dorsal process of a vertebra. The points (main points or auxiliary points) can represent such landmarks. A landmark which lies on (in particular on the surface of) a characteristic anatomical structure of the body part can also represent said structure. The landmark can represent the anatomical structure or only a point or part of it. For instance, a landmark can also lie on the anatomic structure which is in particular a prominent structure. An example of such an anatomic structure is the posterior aspect of the iliac crest. Other landmarks include a landmark defined by the rim of the acetabulum, for instance by the center of the rim. Another example is where a landmark represents the bottom or deepest point of an acetabulum, which is derived from a multitude of detection points. Thus, one landmark can in particular represent a multitude of detection points. As mentioned above, a landmark can represent an anatomical characteristic which is defined based on a characteristic structure of the body part. Additionally, a landmark can also represent an anatomical characteristic defined by a relative movement of two body parts, such as the rotational center of the femur when moved relative to the acetabulum.

A detection point is in particular a point on the surface of the anatomical structure which is detected, for example by a pointer.

Absolute auxiliary point data are also provided in accordance with the invention. These absolute auxiliary point data describe the position of at least one auxiliary point of the pelvis relative to the marker device. Unlike the main points, an auxiliary point lies outside the main plane. If there is more than one auxiliary point, the auxiliary points lie in particular in the so-called auxiliary plane, as will be explained in more detail below. The auxiliary points represent the position of the anatomical characteristics and are in particular (directly or indirectly) defined by landmarks. Both the main points and the auxiliary points are in particular, but not necessarily, points lying on the surface of the pelvis. As mentioned above, the main points and auxiliary points can also be defined indirectly, as will be explained in more detail below, for instance by the rim of the acetabulum or by a rotation center or by landmarks which are symmetrical relative to a plane (for example the main plane or auxiliary plane), again to name but a few examples of indirect definitions of auxiliary points or main points.

According to one example embodiment of the invention, the position of the main points and/or auxiliary points (which represent landmarks) can be detected by a step of contacting the pelvis with the above-mentioned pointer which is handled by a medical assistant and brought into contact with the pelvis. This detection step allows the absolute main point data and absolute auxiliary point data to be provided and in particular does not form a part of the claimed data processing method but may form a part of a general method for determining the position of the main plane. As mentioned above, a multitude of detected points (detection points) on the surface of the pelvis can result in the position of just one landmark and therefore just one main point and/or auxiliary point being detected. A multitude of detection points are for example necessary in order to determine the deepest point in the acetabulum which is a landmark. Another example is when a multitude of detection points are necessary in order to define several positions of the femur relative to the acetabulum. This allows the center of rotation of the relative movement of the femur to be determined. This center of rotation is then a landmark.

The data processing method of the present invention is directed to data processing and in particular does not include steps relating to contacting an anatomical structure.

Relative point data are also provided in accordance with the invention. These relative point data constrain the possible position of the main plane relative to the at least one auxiliary point, in particular relative to only one of the one or more auxiliary points and/or relative to only two of the auxiliary points. The relative point data can in particular constrain the possible positions between a particular auxiliary point of the one or more auxiliary points and another point referred to as the virtual auxiliary point, which is not included in the absolute auxiliary point data. This virtual auxiliary point is in particular a point which is symmetrical to the particular auxiliary point of the one or more auxiliary points with regard to the main plane. Thus, the possible positions of the main plane relative to the at least one auxiliary point are in particular constrained by constraining the possible positions between the at least one auxiliary point and the virtual auxiliary point and/or between the at least one auxiliary point and a virtual main point (see below). An example of such a constraint is that the auxiliary point and its corresponding (symmetrical) virtual point must have a certain distance. A further example of the relative point data is that these data describe an angle between two lines defined by at least three points, at least one of these three points can be a main point (virtual or actual main point). Thus also positional relationships, in which (virtual or actual) main points are involved, can represent constraints for the possible positions of the main plane relative to the at least one auxiliary point.

The constraints described by the relative point data are in particular represented by one or two or more scalar values. These scalar values are in particular used for describing a positional relationship between the main plane and a zero-dimensional or one-dimensional geometrical object, such as a point or line, or between two such geometrical objects. The constraints given by the relative point data are in particular incomplete, i.e. do not allow the exact position of the main plane relative to the at least one auxiliary point to be calculated in a reference system (coordinate system) based only on the position of the at least one auxiliary point and the relative point data. Additional information is necessary. This additional information is for instance the absolute main point data and/or absolute auxiliary point data and/or the pelvis data. The relative point data are in particular incomplete in that at least the position of one main point and at least the position of one auxiliary point are necessary in addition to the relative point data, in order to calculate a position of the main plane. Thus, the relative point data can directly constrain the possible positions of the main plane relative to the at least one auxiliary point by describing a positional relationship (for example a distance or angle) between the at least one auxiliary point and the main plane. The relative point data can also indirectly constrain the positions of the main plane relative to the at least one auxiliary point by describing a positional relationship (for example a distance or angle) between at least one auxiliary point and at least one virtual auxiliary point.

In particular, the relative point data can include but do not need to include geometrical constraints which describe a predetermined positional relationship between planes of the anatomical pelvis, in particular between the auxiliary plane and the main plane and/or between the main plane and the standard plane and/or between the standard plane and the auxiliary plane. The relative point data in particular do not describe that this predetermined positional relationship is a perpendicular relationship. Nevertheless, the constraints allow the number of possible positions to be restricted. The relative point data comprise in particular one scalar value, in particular only one scalar value, if the absolute point data comprise two main points. The relative point data also in particular comprise two scalar values, in particular only two scalar values, if only one main point is provided by the absolute point data. Examples of scalar values are distances and angles.

The relative point data are in particular stored in a data storage (e.g. RAM, ROM, or any database). The relative point data can be generated, preferably before the surgery starts, in particular outside the operating theatre. The relative point data are in particular based on at least one x-ray image of the pelvis. The relative point data are in particular only based on two-dimensional x-ray images. In particular, the relative point data describe constraints which can be derived from (for example based on) a two-dimensional image, in particular only one two-dimensional image (but also possibly two or three or more), for example only one x-ray image. Thus, the relative point data in particular describe positional relationships between geometrical objects, wherein said relationships are present in two dimensions (for example in an image plane). In this way, the data processing method of the present invention can use data which are easily obtained and in particular available before surgery. Thus, it is not necessary to take additional x-ray images, in particular during surgery. It is a particular aspect of the invention that data available before surgery are used to reduce the workload and so aid the surgeon when gathering data from the pelvis by means of a pointer. Furthermore, uncertainties in the position of the determined main plane due to a change in the location of the patient (due to being turned over from the supine position to the lateral position) can be avoided. A specific example of relative point data is the (shortest) distance from an auxiliary point to the main plane. Another example is where there are two auxiliary points which define a line. The relative point data can then describe the distance from one of the auxiliary points to the main plane when following the line and/or can define the angle of the line relative to the main plane. The relative point data may also be based on anatomical knowledge, for instance based on generic or statistical models of the pelvis. Based on these models, for instance distances or angels are derived which are used as relative point data. Furthermore, it is also possible to use, in particular before surgery, a mechanical tool in order to measure the relative point data. For instance, the distance between the two ASIS points may be determined by using a mechanical tool and then the resulting distance may be entered into the system as relative point data. The relative point data can not just describe constraints for the possible positions of the main plane relative to the at least one actual auxiliary point but can in addition describe constraints for the possible positions of the main plane relative to at least one virtual auxiliary point.

As mentioned above, only a minimum number of auxiliary points, preferably but not obligatory in combination with an actual main point can be used as basis for the calculation of the position of the main plane. Thus, there is a minimum of information needed for calculating the position of the main plane. However, of course, more than this minimum information can be used as a basis for the calculation. In particular several actual main points or several actual auxiliary points can represent the basis for the calculation. In that case, a possible error in the calculation of the position of the main plane may be reduced by using this additional information in accordance with general known error reduction methods in case of more information as necessary is available.

The step of calculating the position of the main plane relative to the marker device preferably includes a step of determining a virtual auxiliary point and/or a virtual main point as described above. The position of the main plane is then determined on the basis of the determined virtual main point and/or virtual auxiliary point. There is thus preferably an intermediate step of determining at least one virtual auxiliary point and/or at least one virtual main point (see below).

The majority and in particular preferably all of the actual auxiliary points used for calculating the position of the main plane are preferably outside the main plane but on the same side of the main plane. This is particularly advantageous if the main plane divides the pelvis into parts of at least approximately the same size. This is for instance the case with the mid-sagittal plane (MSP). In this way, it is possible to ensure that the auxiliary points are easily accessible for the surgeon and that the data provided for the data processing method are reliable data, since they were easily and clearly accessible for the surgeon. Another embodiment will be described below, in which the auxiliary points are provided on both sides of the main plane but preferably close to the main plane.

Preferably, the absolute auxiliary point data are used to determine (calculate) at least one additional main point which lies in the main plane and which is the above-mentioned virtual main point. A virtual main point is not included in the absolute main point data, but does lie in the main plane. A virtual main point is in particular not based on the detection of a landmark by means of a pointer. If there are in particular no actual main point or only one or only two actual main points, then there is not enough information available to determine the position of the main plane on the basis of the absolute main point data. Therefore, in accordance with one embodiment of the invention, a particular auxiliary point is used to determine at least one virtual main point. One or more or all of the one or more auxiliary points can be a particular auxiliary point. For the calculation of the virtual main points also already calculated virtual main points and/or actual main points may be used.

The particular auxiliary point can also be used to determine (calculate) at least one additional auxiliary point which lies outside the main plane and which is the above-mentioned virtual auxiliary point. A virtual auxiliary point is not included in the absolute auxiliary point data. A virtual auxiliary point is in particular not based on the detection of a landmark by means of a pointer. The virtual auxiliary point can have a defined positional relationship, in particular a symmetrical relationship with respect to the main plane and preferably also with respect to the particular auxiliary point. The virtual auxiliary point is for example a point which is symmetrical to the particular auxiliary point with respect to the main plane. As mentioned above, the position of the main plane can then be determined on the basis of the particular auxiliary point and the corresponding (symmetrical) virtual auxiliary point. Thus, there is then enough information available to determine the position of the main plane on the basis of the virtual auxiliary point.

As mentioned above, the relative point data include at least one scalar value. This at least one scalar value describes a positional relationship between an auxiliary point and the main plane (for instance, the (shortest) distance from the auxiliary point to the main plane). The scalar value can also describe a positional relationship between two auxiliary points, one of which is a virtual auxiliary point. This virtual auxiliary point is in particular a point at a position which is symmetrical to the other (actual) auxiliary point with respect to the main plane. An example of this is the sinistral and dextral anterior superior iliac spine (ASIS) point. For instance, the dextral ASIS point is the actual auxiliary point and the sinistral ASIS point is the virtual auxiliary point. This situation applies in particular if the patient is lying on their sinistral side. Where here the provision of an "auxiliary point" is mentioned here, it is meant that an actual auxiliary point is provided unless otherwise specified, i.e. an auxiliary point included in the absolute auxiliary point data. In all other cases it may be both (virtual and actual auxiliary point). Where the provision of a "main point" is mentioned here, it is meant that an actual main point is provided unless otherwise specified, i.e. a main point included in the absolute main point data. In all other cases, it may be both (virtual and actual main point). In particular, the absolute main point data describe only those positions of main points which are used to calculate the position of the main plane. In particular, the absolute auxiliary point data describe only those positions of auxiliary points which are used to calculate the position of the main plane. As the actual main and/or auxiliary points preferably do, the virtual main and/or auxiliary points in particular (but not necessarily) represent landmarks. In particular, as far as herein the determination (calculation) of a position of a plane is concerned and a reference is made to main points, if not otherwise specified, this means preferably but not obligatory that not only actual main points can be used for the determination (calculation) but also virtual main points can be used (in addition or exclusively). The same applies if a positional relationship between a main point and any other geometric object (e.g. point or plane) is concerned.

In particular, as far as herein the determination (calculation) of a plane is concerned and a reference is made to auxiliary points, if not otherwise specified or clear from the description, this means preferably but not obligatory that not only actual auxiliary points can be used for the determination (calculation) but also virtual auxiliary points. The same applies if a positional relationship between an auxiliary point and another geometric object (e.g. point or plane) is concerned.

Preferably, the position of the actual auxiliary point in combination with the relative point data allows the position of the virtual auxiliary point to be determined. If the virtual auxiliary point is symmetrical to the main plane with respect to the actual auxiliary point, determining the position of the virtual auxiliary point allows the position of the main plane to be determined.

Also the virtual auxiliary points may be determined indirectly based on the detection of points outside the body part. For instance, the plane on which the patient is lying is determined by using a pointer. Assuming further, the patient is lying in lateral position, e.g. its sinistral ASIS point is in contact with the plane. Furthermore, assuming, the relative point data describe the distance between the sinistral and the dextral ASIS point, then the determined location of the plane on which the patient is lying, allows to calculate, based on the relative point data and the position of the dextral ASIS point (which is provided by the absolute auxiliary point data), the position of the virtual sinistral ASIS point. This virtual auxiliary point may be used for the calculation of the planes in the same manner as the aforementioned actual auxiliary points.

The present invention also preferably uses anatomical knowledge concerning the pelvis. For example, as mentioned above, the relative point data can use this knowledge when referring to statistical models of the pelvis in order to determine distances or angles. Furthermore, this knowledge is preferably used to provide body part data (also referred to as pelvis data). These body part data (pelvis data) constrain the possible relative (anatomical) position between landmarks of the pelvis and/or between the landmarks and the main plane. For instance, body part data (pelvis data) describe that one of the landmarks is more anterior or more posterior or more distal or more proximal or more cranial or more caudal than another landmark. The body part data (pelvis data) can also constrain the possible relative (anatomical) positions between (prominent) anatomical positions of (prominent) anatomical structures such as a crest or an anatomical plane (for example the mid-sagittal plane) or between such structures and landmarks. Thus, the body part data can also be defined in the form of inequality constraints.

In order to use the pelvis data provided, landmark data are preferably provided which link at least some of the main points and/or auxiliary points to the landmarks of the pelvis. The term "at least some" here means in particular at least two or at least three of the points, which can be main points and/or auxiliary points. In other words, the landmark data inform the navigation system as to which (actual or virtual) (main or auxiliary) point represents which landmark. This information is given for at least some of the points.

It is possible, when attempting to determine the position of the main plane on the basis of the provided absolute main point data, the provided auxiliary point data and the provided relative point data, for this attempt to result in more than one possible solution. If more than one solution does result, the provided pelvis data and the provided landmark data are in particular used to discount one or more of the solutions which are not in line with the pelvis data, i.e. which do not correspond to the anatomy of the pelvis and can therefore be discounted. This allows one of the possible solutions for the position of the main plane to be selected on the basis of the provided pelvis data and the provided landmark data. In other words, the solution which is in line with the constraints given by the pelvis data is selected.

As mentioned above, it is not obligatory to provide absolute main point data. However, in that case, preferably at least one virtual main point is calculated based on the absolute auxiliary point data. This calculated at least one virtual main point may be used in the further calculation in the same way as described below for the one or two actual main points. In other words, the provision of actual main points can be replaced by the calculation of virtual main points.

According to a particular embodiment of the present invention, the absolute main point data describe a position of only one main point of the pelvis relative to the marker device or only one virtual main point has been calculated or can be calculated, then two (actual or virtual) main points are in particular missing in order to determine the main plane since only one (actual or virtual) main point is available for the calculation. In this case, the absolute auxiliary point data in particular describe the position of at least two auxiliary points of the pelvis relative to the marker device. As mentioned above, the auxiliary points are outside the main plane. In particular, the actual auxiliary points are on the same side of the main plane. In this way, the data processing method can be based on data which can be easily obtained by a surgeon. In particular, the absolute auxiliary point data describe the position of only two auxiliary points.

In accordance with another embodiment, the absolute main point data describe the position of only two main points of the pelvis relative to the marker device or two virtual main points have been calculated (or can be calculated) or there is one actual main point and one virtual main point, then one additional (virtual or actual) main point is in particular missing in order to determine the main plane since only two (actual or virtual) main points are available for the calculation. In this case, the absolute auxiliary point data preferably describe the position of at least one auxiliary point of the pelvis relative to the marker device, in particular the position of only one auxiliary point of the pelvis relative to the marker device. The auxiliary points are in particular outside the main plane and in particular on the same side of the main plane. Thus, the data processing method can in this case again be performed on the basis of data which are easily generated.

In accordance with another embodiment, the relative position data describe at least one constraint, in particular only one constraint for the possible positions of the main plane relative to the at least one auxiliary point, if the absolute main point data describe the position of two main points, in particular of only two main points. In this case, there is in particular only one auxiliary point.

In accordance with another embodiment, the relative position data describe at least two constraints for the possible positions of the main plane relative to the at least one auxiliary point, if the absolute main point data describe the position of only one main point. In this case, the absolute auxiliary point data describe the position of at least two auxiliary points, in particular of only two auxiliary points.

As mentioned above, the main plane is the mid-sagittal plane in accordance with a preferred embodiment.

In the field of navigated surgery, in particular computer-assisted surgery or image-guided surgery, a reference system (for example a coordinate system) in which the pelvis is located is preferably determined. In order to determine such a coordinate system, two planes defined by the shape of the pelvis are preferably determined. One of these planes is in particular the mid-sagittal plane; the other plane can be the anterior pelvic plane or—as will be explained in more detail below—a spinae joint center plane as a new reference plane referred to as "SJCP". The spinae joint center plane is defined by auxiliary points. In summary, there are preferably at least two planes which have to be determined in order to have an adequate basis for providing navigation information to the surgeon. These two planes and the resulting reference system are in particular used to define the position and in particular the orientation of the acetabulum, in particular for hip surgery.

The present invention also relates to a data processing method which includes the above-mentioned data processing method and not only allows the position of the main plane of the pelvis but also an auxiliary plane of the pelvis to be determined.

The data processing method for determining the main plane and the auxiliary plane preferably uses the above-mentioned data processing method in order to determine the main plane. The above-mentioned data processing method will therefore be referred to as the first data processing method. The data processing method for determining both the main plane and the auxiliary plane will be referred to as the second data processing method. The second data processing method uses the following approach for determining the auxiliary plane. Absolute auxiliary point data are provided which describe the position of at least two of the auxiliary points of the pelvis relative to the marker device. Thus, contrary to the first data processing method, there is preferably a minimum of two auxiliary points, the position of which is known from the absolute auxiliary point data. The auxiliary points are preferably outside the main plane. The auxiliary points are in particular on the same side of the main plane. Preferably, at least one of the at least two auxiliary points is used for calculating the position of the main plane. In accordance with another embodiment, the at least two auxiliary points are used for calculating the position of the main plane. Data are also provided which are referred to as relative auxiliary plane data. These auxiliary plane data describe the positional relationship between the auxiliary plane and the main plane. Furthermore, it is assumed that the auxiliary points lie within the auxiliary plane.

In accordance with the second data processing method, the provided relative auxiliary plane data are preferably used to calculate the position of the auxiliary plane on the basis of the assumption that the at least two auxiliary points lie within the auxiliary plane. In other words, the auxiliary plane is determined in such a way that it includes the at least two auxiliary points and fulfils the predetermined positional relationship with respect to the main plane, said relationship being known from the relative auxiliary plane data.

One example of the predetermined positional relationship is a particular angle between the main plane and the auxiliary plane. The angle can in particular be within the range of 30° to 150°. The predetermined positional relationship can in particular be such that the auxiliary plane is perpendicular to the main plane.

The invention is also directed to a third data processing method which comprises the second data processing method explained above. The third data processing method is a method for determining the position of the main plane and of a standard plane, wherein the position of the auxiliary plane has been determined by the second data processing method. The auxiliary points lying in the auxiliary plane are in particular landmarks of the pelvis. Examples of auxiliary points will be given below.

In accordance with the third data processing method, relative standard plane data are also provided. The relative standard plane data describe the expected relative positional relationship between the auxiliary plane and the standard plane. The expected relative positional relationship is a positional relationship which can correspond to an average positional relationship derived from a statistical analysis of the positional relationship between the auxiliary plane and the standard plane for a plurality of different pelvises. In particular, the average positional relationship which results from this statistical analysis represents the expected positional relationship. Any kind of (statistical) method for determining an average can be applied, for instance the arithmetic mean or the median or the mode. A generic model of the pelvis can also be used to determine the relative positional relationship between the auxiliary plane of the generic model and the standard plane of the generic model. This positional relationship also represents an example of an expected positional relationship.

In accordance with the third data processing method, the position of the standard plane is determined on the basis of the position of the auxiliary plane (determined using the second data processing method) and on the basis of the relative standard plane data. For instance, the relative standard plane data describe an angle between the position of the auxiliary plane and the position of the standard plane. Thus, the determined position of the auxiliary plane allows the position of the standard plane to be calculated on the basis of the standard plane data. A standard plane is in particular a plane with respect to which the position of the femoral shaft and/or the position (and/or orientation) of the acetabulum is (usually) described.

As mentioned above, the auxiliary points can represent landmarks in any of the data processing methods described above (i.e. the first, second and/or third data processing method). Examples of landmarks represented by the auxiliary points include the sinistral ASIS point or dextral ASIS point. The auxiliary points can alternatively or additionally represent a landmark which is defined by the acetabulum and/or by a partial (surface) point of the acetabulum. The auxiliary point can then in particular be the rotational center or the deepest part of the acetabulum or the most proximal part of the acetabulum. The main plane in any of the data processing methods described above (i.e. the first, second or third data processing methods) can for example be the mid-sagittal plane. The standard plane as described with respect to the third data processing method can for example be the anterior pelvic plane. The relative standard plane data described in connection with the third data processing method describe in particular the angle between the anterior pelvic plane and the auxiliary plane. The auxiliary plane (for example the SJCP) is in particular a plane described by the sinistral and dextral ASIS point and an auxiliary point defined by the acetabulum or a point or part of the acetabulum. The auxiliary plane is in particular such that the auxiliary plane and the anterior pelvic plane intersect each other along a line connecting the sinistral and the dextral anterior superior iliac spine landmarks of the pelvis. The present application is also directed to an independent invention which is directed to a data processing method which relies on the relative standard plane data which describe the relative position between the anterior pelvic plane (APP) and the spinae joint center plane (SJCP). Thus, preferably any data processing method or system or computer etc. is a subject-matter of the present invention which relies on this kind of standard plane data. The inventors of the present invention have first found that the APP and SJCP have a statistically stable relative positional relationship which may be used in any kind of data processing methods which processes data related to the pelvis. Therefore, the present application is also directed to such an independent invention which may be a subject-matter of a later divisional application. These data processing methods are in particular directed to a calculation of positions, in particular orientations of planes or parts or points of the pelvis for computer aided navigation in surgery (image guided surgery). Such a data processing method is in particular as follows: A data processing method for determining the position of a plane or a part or a point of pelvis which comprise the steps of: providing relative standard plane data which describe the expected positional relationship between the SJCP and the APP; and determining the position of the APP on the basis of the position of the SJCP and the relative standard plane data.

The following embodiment can be combined with the aforementioned methods or can also represent an independent embodiment of the invention. In accordance with this embodiment, additional auxiliary points are determined which are in particular symmetrical to another auxiliary point if the main plane is taken as the plane of symmetry. Said other auxiliary point (which corresponds to the additional auxiliary point) is referred to as the symmetrical auxiliary point. The (at least one) symmetrical auxiliary point is included in the absolute auxiliary point data, whereas the (at least one) additional auxiliary point is not included. As an independent embodiment of the invention, the (at least one) symmetrical auxiliary point is provided in a step of the independent data processing method. In accordance with this embodiment, relative auxiliary point data are provided. These relative auxiliary point data describe at least one constraint for possible positions of the additional auxiliary point relative to its corresponding symmetrical auxiliary point. When the symmetrical auxiliary point is on one side of the main plane, the corresponding additional auxiliary point is in particular on the other side. In accordance with this embodiment, candidate point data are provided. The candidate point data describe the position of a candidate point with respect to the marker device. These candidate points are candidates for the additional auxiliary point. New candidate point data which describe the position of new candidate points relative to the marker device are preferably provided in steps. All the candidate points provided are preferably on the same side of the main plane. The new candidate point data are preferably received in steps, such that candidate point data are provided in steps. A candidate point received in the current step is referred to as the current candidate point. In accordance with this embodiment, the next step consists of checking whether the position of the current candidate point (i.e. the new candidate point) complies with the at least one constraint. The at least one constraint is described by the relative auxiliary point data as mentioned above. An example of the constraint is in particular a distance between the symmetrical auxiliary point and its corresponding additional auxiliary point.

After the checking step, the current candidate point (new candidate point) is preferably accepted as an additional auxiliary point if the position of the current candidate point complies with the at least one constraint defined by the relative auxiliary point data, i.e. if the position of the current candidate point is a possible position. If the position of the current candidate point does not comply with the at least one constraint, then the aforementioned steps (of providing and checking) are repeated. Since the additional auxiliary point is symmetrical to the symmetrical auxiliary point with respect to the main plane, the position of the main plane can be determined on the basis of the additional auxiliary point and the symmetrical auxiliary point. The new candidate point data are preferably generated by detecting a point which contacts an additional anatomical structure which is symmetrical to another anatomical structure (referred to as the symmetrical structure). This structure is in particular a prominent structure (for example a rim or crest). A point detected on the symmetrical structure corresponds to the symmetrical auxiliary point. A plurality of points detected on the additional anatomical structure are candidate points for the additional auxiliary point. During the movement of the pointer along the additional anatomical structure, new candidate points are generated in steps. In order to guide the user during the movement of the pointer, indication data are preferably provided. Both the additional auxiliary point and the symmetrical auxiliary point are preferably determined on the basis of the above-mentioned detection points (representing detected landmarks) and in particular not on virtual auxiliary points.

In accordance with another embodiment, the aforementioned method comprises additional steps which relate to generating indication data. These indication data are in particular based on the result of the checking step and indicate whether the position of the candidate point complies with the at least one constraint. These indication data are preferably used by an indication method which comprises the aforementioned data processing method and which generates indication signals on the basis of the indication data in order to inform a user (surgeon) as to whether the current candidate point complies with the constraint. Preferably, a deviation between a scalar value describing the constraint (for instance a distance) and a scalar value describing the position of the current candidate point relative to a main point or the particular auxiliary point is calculated. The result of the calculation is then preferably part of the indication data and is thus also indicated to the user as part of the indication signal. A surgeon can use the above-mentioned data processing method as an assistance in finding an auxiliary point when scanning the pelvis with a pointer.

The present invention is also directed to a program which, when it is running on a computer or is loaded onto a computer, causes the computer to perform the data processing method as described in any one of the preceding embodiments. The present invention is also directed to a program storage medium (for instance a CD, ROM, RAM, harddrive, etc.) on which the program is stored. The present invention also relates to a computer on which the program is running, by which the program is executed or on which the program is loaded. This computer in particular comprises a memory which stores the program. The present invention is also directed to a signal wave, in particular a digital signal wave, which carries the information represented by the program. A signal wave carries the program for example during a download process when downloading the program via the internet.

The present invention is also directed to a navigation system for computer-assisted surgery. This navigation system preferably comprises the aforementioned computer for processing the data provided in accordance with the data processing method as described in any one of the preceding embodiments. Preferably, the navigation system comprises a detection device for detecting the position of the detection points which represent the main points and auxiliary points, in order to generate detection signals and to supply the detection signals generated to the computer such that the computer can determine the absolute main point data and absolute auxiliary point data on the basis of the detection signals received. In this way, the absolute point data can be provided to the computer. The navigation system also preferably comprises a user interface for receiving the calculation results from the computer (for example the position of the main plane, the position of the auxiliary plane and/or the position of the standard plane). The user interface provides the received data to the user as information. Examples of a user interface are a monitor or a loudspeaker. The user interface can use any kind of indication signal (for example a visual signal, an audio signal and/or a vibration signal).

Where data are described here as being "provided", this means that they are ready for use by the method in accordance with the invention. The data can achieve this state of being "provided" by for example being detected or captured (for example by a detection device) or by being inputted (for example via interfaces) or by being determined on the basis of input signals or detection signals or input data. The data can also have this state by being stored in a memory (for example a ROM, CD and/or hard drive) and thus ready for use within the framework of the method in accordance with the invention.

In the following detailed description, other features of the present invention are disclosed. The features of different embodiments can be combined.

Figure 1:
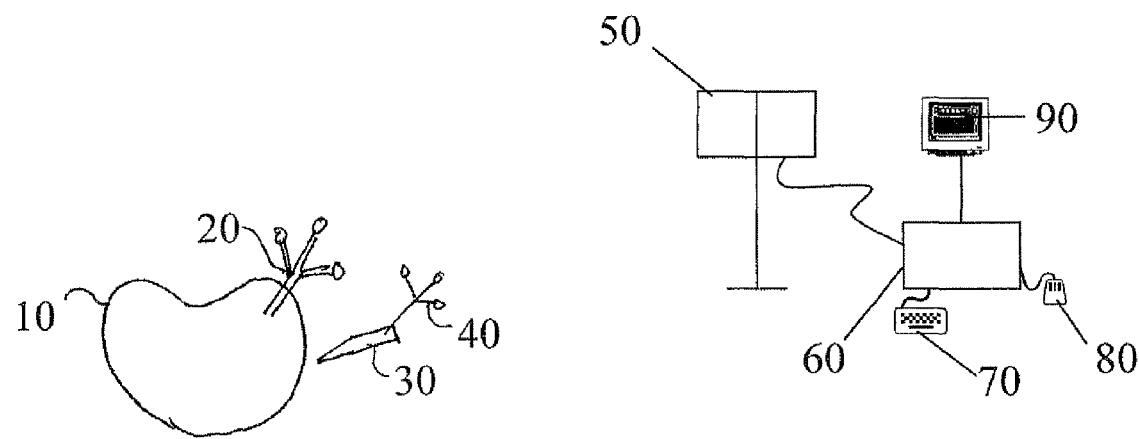
FIG. 1 shows a navigation system in accordance with the invention.

FIG. 1 schematically shows a pelvis 10. Attached to the pelvis 10 is a reference star 20. There is a fixed spatial relationship between the reference star 20 and the pelvis 10. A surgeon can contact parts, in particular landmarks, of the pelvis 10 by means of the tip of a pointer 30. Attached to the pointer 30 are markers, in particular another reference star 40. The location of the reference stars 20 and 40 (and the corresponding markers) can be detected by the detection device 50. The process of contacting the pelvis with the pointer and detecting the markers of the pointer is also referred to here as "scanning". The detection device 50 supplies the detection signals to the computer 60. The computer 60 includes a database which stores the relative spatial relationship between the markers of the pointer and the tip of the pointer. In the computer 60, the absolute point data are then determined on the basis of the detection signals received from the detection device 50. The relative point and/or pelvis data can be input or can be stored in the database. Due to this determination, the absolute point data are available and thus provided.

A keyboard 70 and mouse 80 and a monitor 90 are for example connected to the computer 60. The monitor 90 serves to display information to the user such as the results of the processing performed in accordance with a data processing method of the invention and/or indication signals as already mentioned above.

Figure 2:
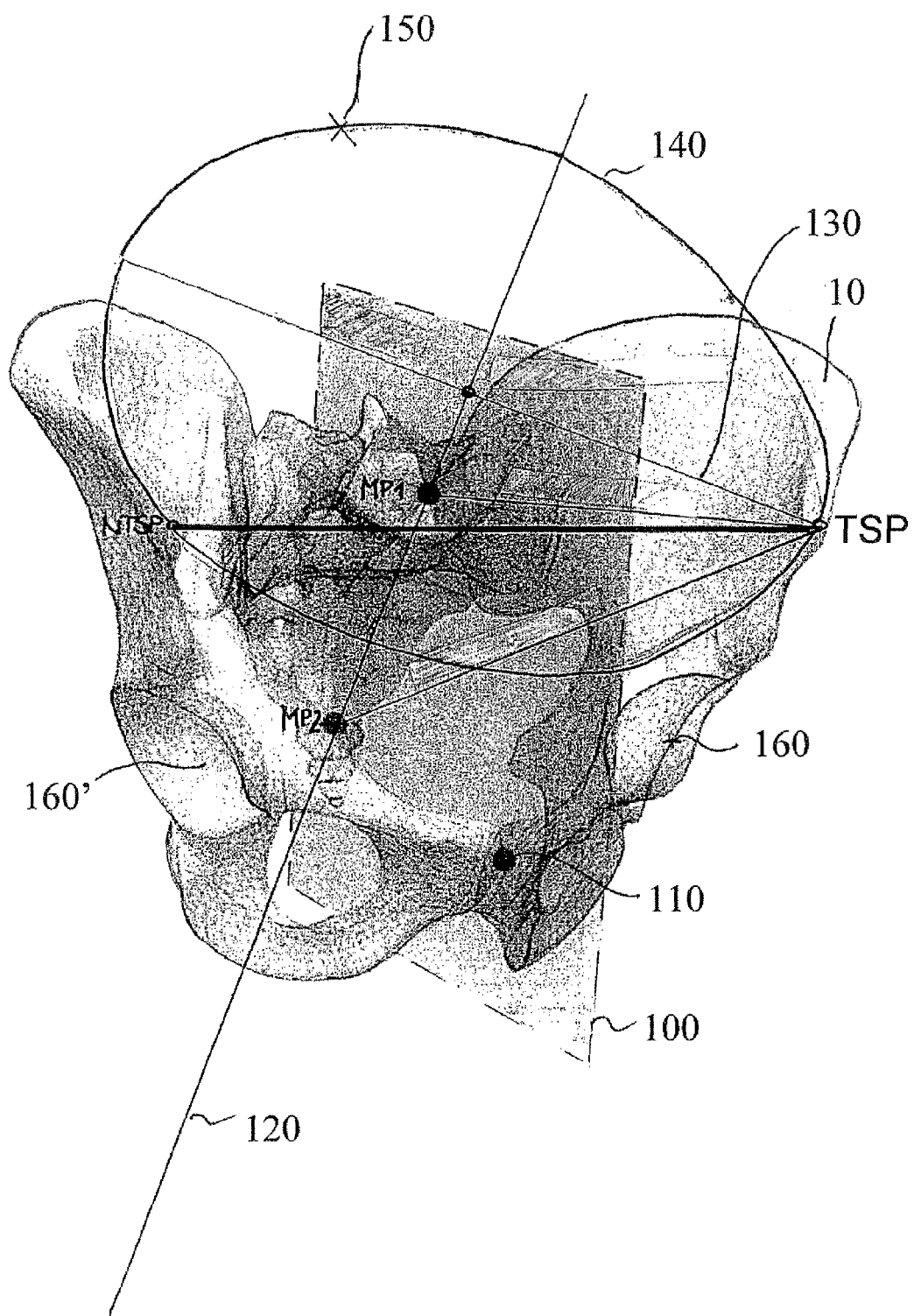
FIG. 2 shows the use of main and auxiliary points for determining the mid-sagittal plane.

FIG. 2 shows the pelvis 10 in more detail. The attached reference star 20 is not shown. FIG. 2 also shows a landmark TSP which is the ASIS point. This landmark TSP has been scanned by the pointer 30, and the corresponding position information has been supplied to the computer 60 of the navigation system. The navigation system comprises the detection device 50, the computer 60 and the monitor 90. Two landmarks MP1 and MP2 have also been scanned by the pointer 30. These landmarks MP1 and MP2 lie in the mid-sagittal plane 100. For instance, in the following the points MP1 and MP2 are assumed to be points on the sacrum and lumbar spine. The point TSP is an example of an auxiliary point, and the points MP1 and MP2 are examples of main points. Another main point would be the pubic landmark 110. However, in the following, it is assumed that the absolute main point data describe only the position of MP1 and MP2 and that the absolute auxiliary point data describe only the position of TSP. In the following, it will be described how the position of the main plane (the mid-sagittal plane 100) is determined on the basis of only two main points and only one auxiliary point.

In accordance with one possible procedure, a line 120 is determined by MP1 and MP2. A line 130 is drawn from the point TSP and intersects the line 120 at a right angle. Thus, the line 130 is perpendicular to the line 120. The intersection between the line 120 and the line 130 defines the center of a circle 140. The circle 140 includes the point TSP and another point NTSP. The point NTSP is a virtual auxiliary point (i.e. NTSP has not been scanned). The point NTSP is symmetrical to the point TSP with respect to the mid-sagittal plane 100. In other words, if the point TSP is mirrored in the mid-sagittal plane 100, this would result in the point NTSP. The point NTSP is the solution which is to be found. Relative point data are used to find the point NTSP. The relative point data describe the distance between NTSP and TSP. This distance can for example be derived from an x-ray of the pelvis 10. The point NTSP has to be on the circle 140 and has to fulfill the constraint, i.e. has to have the predetermined distance from the point TSP. There are two possible solutions for these constraints, namely NTSP and the point 150. The point 150 is an incorrect solution. The pelvis data are used to discount the incorrect solution 150 from the two possible solutions. The pelvis data describe in particular anatomical characteristics of the pelvis. These data describe in particular that the point NTSP is more anterior than the point MP1. The point 150, however, is more posterior than MP1. Therefore, this possible solution can be discounted. The solution NTSP is therefore selected, since this point complies with the anatomical characteristic that the solution has to be more anterior than MP1. The constraint that NTSP has to be more anterior than MP1 represents an example of the possible relative positions between MP1 and NTSP$|_{[HAM2]}$. These possible relative positions are constraints described by the pelvis data. The circle 140 is incidentally also perpendicular to the line 120.

In accordance with another possible data processing method, a sphere is constructed which has a radius corresponding to the distance between MP1 and TSP. The center of this sphere is located at the point MP1. A second sphere is also constructed which has a radius corresponding to the distance between MP2 and TSP. The center of the second sphere is located at the point MP2. The intersection between these two spheres is the circle 140 which corresponds to a multitude of possible solutions for the location of the point NTSP. In the same way as mentioned above, this multitude of possible solutions is firstly restricted to the point NTSP and the point 150 by using the constraint which defines the distance between NTSP and TSP. In a subsequent step, the pelvis data are then used to discount the point 150 from the possible solutions, such that the point NTSP remains as the only possible solution.

As mentioned above, NTSP and TSP are symmetrical to each other with respect to the mid-sagittal plane. Therefore, the mid-sagittal plane is defined as being perpendicular to the line which connects NTSP and TSP, hence the mid-sagittal plane is determined.

In accordance with another preferred step, another plane—the auxiliary plane—is determined, with the aim of defining a coordinate system in which the pelvis rests. For this purpose, another auxiliary point 160 is provided. To this end, the landmark corresponding to the auxiliary point 160 is preferably scanned by the pointer 30. The auxiliary plane is then defined as being perpendicular to the mid-sagittal plane 100 and including the two auxiliary points TSP and 160. The auxiliary point 160 is preferably based on the acetabulum. It can for example be the rotational center of the femoral head in the acetabulum or the bottom of the acetabulum or the center of the rim of the acetabulum, to name but a few examples. The inventors of the present application have found that there is a reliable and fixed spatial relationship between a standard plane (APP) and the aforementioned auxiliary plane which includes a landmark defined by the acetabulum and the ASIS point as another auxiliary point. The point TSP preferably corresponds to the ASIS point, in which case the auxiliary plane has a defined positional relationship to the anterior pelvic plane (APP) which is often used as a reference for defining the orientation of the acetabulum. This standard plane is also perpendicular to the mid-sagittal plane and has an angle of about 40° with respect to the aforementioned plane which includes the ASIS point and the acetabulum landmark point. This auxiliary plane is also referred to here as the spinae joint center plane (SJCP).

In the manner described above, at least two planes are defined which allow a coordinate system to detected defined. The planes can for example be the mid-sagittal plane and the auxiliary plane (in particular the SJCP) and/or can be the mid-sagittal plane and the APP.

In the following, the data processing method is described for the scenario in which there is only one main point on the mid-sagittal plane. In this case, the relative point data preferably comprise two constraints or more specifically two scalar values. One scalar value describes the distance between the point NTSP and the point TSP. The other scalar value describes the distance between the acetabular or auxiliary point 160 and the symmetrical acetabular or auxiliary point 160'. In other words, the symmetrical acetabulum 160' is symmetrical with respect to the mid-sagittal plane, i.e. the point 160' is a mirrored point of the acetabular point 160.

The two scalar values, i.e. the two distances, are in particular known from x-ray images. The distance between the point TSP and the point 160 is also known due to the absolute auxiliary point data. In a subsequent step, a line can be constructed on the basis of the TSP point and the point 160. This line crosses the mid-sagittal plane 100. The distance between the point 160 and the mid-sagittal plane 100 along this line can be calculated on the basis of geometric laws by using the aforementioned two distances between the point TSP and the point NTSP and between the point 160 and the point 160'. Thus, the position at which the line which includes the point TSP and the point 160 crosses the mid-sagittal plane can be calculated. Thus, a second point on the mid-sagittal plane is known. The procedure already known from the above description can then be applied in order to determine the position of the point NTSP or the point 160'. If these positions are known, then the mid-sagittal plane is defined as being perpendicular to the line connecting the point NTSP and the point TSP and/or perpendicular to the line connecting the point 160' and the point 160. The SJCP or the APP can also then be calculated in the manner described above.

Using the SJCP to define a coordinate system can be advantageous, since the APP might be less reliably determined by scanning, i.e. using a pointer to detect the landmarks on the APP. The pubic landmark 110 in particular can introduce uncertainties into the method due to differing amounts of fat and other soft tissue above the pubic area. These tissues can prevent the position of the point 110 from being accurately detected by means of a pointer.

The coordinate systems defined in accordance with the method of the present invention can be used for registration and also for other tasks within planning and navigation steps. The method of the present invention (i.e. the data processing method) is in particular used for planning surgery and for computer-assisted navigation. Because of the reliable and consistent relationship between a coordinate system defined by the mid-sagittal plane and SJCP and standard coordinate systems, all information can be transferred back and forth between the coordinate systems.

In accordance with another embodiment, one main point is scanned by the pointer on the mid-sagittal plane. In other words, one main point is provided to the data processing method. One additional (first) point on a structure, in particular a prominent structure, of the pelvis is determined as an auxiliary point (symmetrical auxiliary point). An example of the prominent structure is the posterior aspect of the iliac crest. The data processing method of the present invention, performed in particular on the navigation system of the invention, then assists the user in finding another (second) auxiliary point by issuing the indication signal mentioned above. This second point is symmetrical to the first point with respect to the mid-sagittal plane. For this purpose, the navigation system shows additional information (indication signals) such as distance values or angles. The rationale behind this approach is that the user is assisted in finding the second point which has the same relationship (for example distance/angle) to the mid-sagittal plane as the first point. The user can thus proceed along the prominent structure until the system informs the surgeon that the desired relationship has been found. In general, this approach can be used to find new reference points (new auxiliary points) on an anatomical object from given points and the specific relationships (geometric features/constraints) between the given point and the points to be determined. The navigation system according to the invention assists in finding the new points (new auxiliary points) by providing information concerning the geometric features/constraints. The user can thus find these new auxiliary points by locating them on a prominent structure. This prominent structure can be close to the mid-sagittal plane.

The above-mentioned embodiment can in particular be used in the case of lateral pelvic registration. The embodiment can be used to find a second point which lies symmetrical to the first point with respect to the mid-sagittal plane. The line between these two points represents the medial-lateral direction. This can be used as an additional constraint. It provides not only a one-dimensional but a two-dimensional constraint. Thus, only one point on the mid-sagittal plane is required in this case. In the same way as in the previous embodiments, additional information (relative point data and/or pelvis data) can be used to make the registration more robust.

The invention claimed is:

1. A computer-implemented method for determining a mid-sagittal plane position of a mid-sagittal plane of a pelvis by a computer comprising a non-transient memory, wherein the mid-sagittal plane is a plane which can be described by anatomical landmarks of the pelvis, the method comprising:

providing absolute auxiliary point data to the computer, wherein the absolute auxiliary point data relates to an auxiliary point position of at least one actual auxiliary point of a plurality of actual auxiliary points of the pelvis relative to a marker device, the marker device comprising one or more markers arranged in a predetermined spatial relationship representative of the marker device wherein data representative of the spatial relationship is stored in the memory, the plurality of actual auxiliary points being outside the mid-sagittal plane and representing first anatomical landmarks of the pelvis;

providing relative point data to the computer, wherein the relative point data constrain possible positions of the mid-sagittal plane relative to the at least one actual auxiliary point;

providing absolute main point data to the computer, wherein the absolute main point data relate to an absolute main point position of one or two actual main points of the pelvis relative to the marker device, said one or two actual main points lying in the mid-sagittal plane and representing a second anatomical landmark of the pelvis, the absolute auxiliary point data and the absolute main point data having been generated by detection, the detection comprising a step of contacting the pelvis;

using a computer including a processor and memory to perform at least one of:

a) calculating, by the processor, a virtual main point position of at least one virtual main point relative to the marker device, said at least one virtual main point being in the mid-sagittal plane and being calculated by the processor based on the absolute auxiliary point data and the relative point data, wherein the relative point data constrain possible relative positions between the mid-sagittal plane and two particular auxiliary points of the plurality of actual auxiliary points, the relative point data prescribing an angle between the mid-sagittal plane and a line crossing the mid-sagittal plane, wherein the line is defined by the two particular auxiliary points and the two particular auxiliary points are on the same side of the mid-sagittal plane; and b) determining, by the processor, at least one virtual auxiliary point on the basis of the relative point data and the absolute main point data and selectively on the basis of the calculated virtual main point position, a virtual auxiliary point position of the virtual auxiliary point being symmetrical to a position of a particular auxiliary point of the plurality of actual auxiliary points with respect to the mid-sagittal plane, wherein the relative point data constrain possible relative positions between the particular auxiliary point of the one or more auxiliary points and the mid-sagittal plane by defining a distance between the mid-sagittal plane and the particular auxiliary point, wherein the definition of the distance is determined by a shortest distance between the mid-sagittal plane and one actual auxiliary point of the plurality of actual auxiliary points, and/or by defining a distance between the virtual auxiliary point and the particular auxiliary point;

calculating by the processor the mid-sagittal plane position relative to the marker device, wherein the calculation uses the relative point data, the auxiliary point data, and the provided main point data as well as at least one of the calculated at least one virtual main point position and the calculated at least one virtual auxiliary point position;

generating an indication signal for providing information to a user based on the calculated mid-sagittal plane and the data representative of the spatial relationship; and/or using the position of the mid-sagittal plane for determining a coordinate system with respect to which a position of an object can be defined.

2. The method according to claim 1, wherein the at least one virtual main point is not included in the absolute main point data and the at least one virtual auxiliary point is not included in the absolute auxiliary point data.

3. The method according to claim 1, wherein the relative point data describe at least one scalar value used for describing positional relationships between a particular auxiliary point of the one or more auxiliary points and the virtual main point and/or between the particular auxiliary point and the virtual auxiliary point, the virtual auxiliary point position of the virtual auxiliary point being in particular symmetrical to the virtual auxiliary point position of the particular auxiliary point with respect to the mid-sagittal plane, and/or between one or more of the auxiliary points and the mid-sagittal plane.

4. The method according to claim 1, further comprising:
providing body part data to the computer, wherein the body part data constrains the possible relative positions between landmarks of the body part and/or between the landmarks and the mid-sagittal plane;
providing landmark data to the computer, wherein the landmark data respectively correlate at least some of the actual and/or virtual main points and/or auxiliary points with at least some of the landmarks of the body part; and
if more than one solution for calculating the position of the mid-sagittal plane is possible, selecting one of the possible solutions for the position of the mid-sagittal plane on the basis of the landmark data and body part data.

5. The method according to claim 1, wherein all of the actual auxiliary points described by the absolute auxiliary point data and used for calculating the position of the mid-sagittal plane are outside the mid-sagittal plane but on a common side of the mid-sagittal plane.

6. The method according to claim 3, wherein if the main point position of only one main point of the body part relative to the marker device is available for the calculation, then the absolute auxiliary point data describe the position of at least two auxiliary points of the body part relative to the marker device, the at least two auxiliary points being outside the mid-sagittal plane; and if the main point positions of only two main points of the body part relative to the marker device are available for the calculation, then the absolute auxiliary point data describe the auxiliary point position of at least one auxiliary point of the body part relative to the marker device, the at least one auxiliary point being outside the mid-sagittal plane.

7. The method according to claim 6, wherein the at least one scalar value represents a distance or an angle.

8. The method according to claim 6, wherein the relative point data describe at least one constraint for the possible constrained positions of the mid-sagittal plane relative to the at least one auxiliary point, if there are two main points; and describe at least two constraints for the constrained positions of the mid-sagittal plane relative to the at least one auxiliary point, if there is only one main point.

9. A method which includes the data processing method of claim 1 and which is a method for determining the mid-sagittal plane position of the mid-sagittal plane of the pelvis and of an auxiliary plane of the pelvis, wherein in order to determine the mid-sagittal plane, the data processing method of claim 1 is performed, and in order to determine the auxiliary plane, absolute auxiliary point data describe the auxiliary point position of at least two of the auxiliary points of the body part relative to the marker device, the at least two auxiliary points being outside the mid-sagittal plane; further comprising the step of providing relative auxiliary plane data which describe a predetermined positional relationship between the auxiliary plane and the mid-sagittal plane;
wherein the auxiliary plane position is determined by assuming that the at least two auxiliary points lie in the auxiliary plane, and is determined on the basis of the relative auxiliary plane data.

10. The data processing method of claim 9 further including determining a position of a standard plane, further comprising:
providing relative standard plane data to the computer, wherein the relative standard plane data describe an expected positional relationship between the auxiliary plane and the standard plane; and
processing the position of the auxiliary plane and the relative standard plane data to determine the position of the standard plane.

11. The method according to claim 1, wherein one of the landmarks represented by one of the auxiliary points comprises:
the sinistral or dextral anterior superior iliac spine landmark; and/or
the standard plane is the anterior pelvic plane; and/or
the standard plane data describe the angle between the anterior pelvic plane and the auxiliary plane; and/or
the anterior pelvic plane and the auxiliary plane intersect each other along a line connecting the sinistral and the dextral anterior superior iliac spine landmarks of the body part; and/or
another auxiliary point represents a landmark defined by the acetabulum or a point or a part of the acetabulum.

12. The method according to claim 1, further comprising:
providing at least one auxiliary point to the computer;
providing relative auxiliary point data to the computer, wherein the relative auxiliary point data describe at least one constraint which limits the possible positions for an additional auxiliary point, the additional auxiliary point being symmetrical to one of the plurality of auxiliary points with respect to the mid-sagittal plane; and
providing candidate point data to the computer in steps, wherein in each step, the position of a new candidate point is described by the candidate point data, wherein in the current step, the following steps are performed:

a) providing new candidate point data to the computer, wherein the new candidate point data describe a new candidate point position that is a relative position of a new candidate point with respect to the marker device, the new candidate point position being a new candidate for an additional auxiliary point position corresponding to the additional auxiliary point;

b) checking by the computer whether the positions of the new candidate point position complies with the at least one constraint described by the relative auxiliary point data;

c) repeating steps a) and b) if the new candidate point position does not comply with the at least one constraint, or accepting the new candidate point as an additional auxiliary point if the new candidate point position does comply with the at least one constraint.

13. A program embodied on a non-transitory computer-readable medium, wherein when the program is running on a computer or is loaded onto a non-transient memory of the computer, causes the computer to perform data processing steps for determining a mid-sagittal plane position of a mid-sagittal plane of a pelvis, wherein the mid-sagittal plane is a plane which can be described by anatomical landmarks of the pelvis, the data processing steps comprising:

providing absolute auxiliary point data which describe an absolute auxiliary point position of at least one actual auxiliary point of a plurality of actual auxiliary points of the pelvis relative to a marker device, the marker device comprising one or more markers arranged in a predetermined spatial relationship representative of the marker device and being stored in the memory, the plurality of actual auxiliary points being outside the mid-sagittal plane and representing first anatomical landmarks of the pelvis;

providing relative point data which constrain possible positions of the mid-sagittal plane relative to the at least one actual auxiliary point;

providing absolute main point data which describe an absolute main point position of one or two actual main points of the pelvis relative to the marker device, said one or two actual main points lying in the mid-sagittal plane and representing a second anatomical landmark of the pelvis;

at least one of:

a) calculating by the computer at least one virtual main point position of at least one virtual main point relative to the marker device, said at least one virtual main point being in the mid-sagittal plane and being calculated based on the absolute auxiliary point data and the relative point data, wherein the relative point data constrain possible relative positions between the mid-sagittal plane and two particular auxiliary points of the plurality of actual auxiliary points, the relative point data prescribing an angle between the mid-sagittal plane and a line crossing the mid-sagittal plane, wherein the line is defined by the two particular auxiliary points and the two particular auxiliary points are on the same side of the mid-sagittal plane; and b) determining at least one virtual auxiliary point on the basis of the relative point data and the absolute main point data and selectively on the basis of the calculated virtual main point position, a virtual auxiliary point position of the virtual auxiliary point being symmetrical to a position of a particular auxiliary point of the plurality of actual auxiliary points with respect to the mid-sagittal plane, wherein the relative point data constrain possible relative positions between the particular auxiliary point of the one or more auxiliary points and the mid-sagittal plane by defining a distance between the mid-sagittal plane and the particular auxiliary point, wherein the definition of the distance is determined by a shortest distance between the mid-sagittal plane and one actual auxiliary point of the plurality of actual auxiliary points, and/or by defining a distance between the virtual auxiliary point and the particular auxiliary point; and calculating by the computer the mid-sagittal plane position relative to the marker device, wherein the calculation uses the relative point data, the auxiliary point data, the predetermined spatial relationship representative of the marker device, and the provided main point data as well as at least one of the calculated at least one virtual main point position and the calculated at least one virtual auxiliary point position.

14. A navigation system for computer-assisted surgery, comprising:

a detection device for detecting positions of main and auxiliary points and for generating detection signals which represent positions for the main and auxiliary points; and a computer including a processor and a memory; and logic stored in the memory and executable by the processor, the logic when executed by the processor causes the computer to perform a data processing method for determining a mid-sagittal plane position of a pelvis, wherein the mid-sagittal plane is a plane which can be described by anatomical landmarks of the pelvis, the data processing method comprising:

providing absolute auxiliary point data to the computer, wherein the absolute auxiliary point data describes a position of at least one actual auxiliary point of a plurality of actual auxiliary points of the pelvis relative to a marker device, the marker device comprising one or more markers arranged in a predetermined spatial relationship representative of the marker device and being stored in the memory, the plurality of actual auxiliary points being outside the mid-sagittal plane and representing first anatomical landmarks of the pelvis;

providing relative point data to the computer, wherein the relative point data constrains possible positions of the mid-sagittal plane relative to the at least one actual auxiliary point;

providing absolute main point data to the computer, wherein absolute main point data describes a position of one or two actual main points of the pelvis relative to the marker device, said one or two actual main points lying in the mid-sagittal plane and representing a second anatomical landmark of the pelvis;

at least one of:

a) calculating a virtual main point position of at least one virtual main point relative to the marker device, said at least one virtual main point being in the mid-sagittal plane and being calculated based on the absolute auxiliary point data and the relative point data, wherein the relative point data constrain possible relative positions between the mid-sagittal plane and two particular auxiliary points of the plurality of actual auxiliary points, the relative point data by defining an angle between the mid-sagittal plane and a line crossing the mid-sagittal plane, wherein the line is defined by the two particular auxiliary points and the two particular auxiliary points are on the same side of the mid-sagittal plane; and b) determining at least one virtual auxiliary point data on the basis of the relative point data and the absolute main point data and selectively on the basis of the calculated virtual main point position, a virtual auxiliary point position of the virtual auxiliary point being symmetrical to the position of a particular auxiliary point of the plurality of actual auxiliary points with respect to the mid-sagittal plane wherein the relative point data constrain possible relative positions between the particular auxiliary point of the one or more auxiliary points and the mid-sagittal plane by defining a distance between the mid-sagittal plane and the particular auxiliary point, wherein the definition of the distance is determined by a shortest distance between the mid-sagittal plane and one actual auxiliary point of the plurality of actual auxiliary points, and/or by defining a distance between the virtual auxiliary point and the particular auxiliary point; and calculating by the computer the mid-sagittal plane position relative to the marker device, wherein the calculation uses the relative point data, the auxiliary point data, the predetermined spatial relationship, and the provided main point data as well as at least one of the calculated at least one virtual main point position and the calculated at least one virtual auxiliary point position.

15. A computer-implemented method for determining the position of a mid-sagittal plane of a pelvis, the method comprising:

generating detection signals by detecting a pointer, said pointer contacting a body part;

determining on the basis of the detection signals, an absolute main point data and absolute auxiliary point data, and then performing the method according to claim 1 on the basis of the determined absolute main point data and absolute auxiliary point data.

16. A computer comprising the program embodied on a non-transitory computer-readable medium according to claim 13.

17. The method according to claim 1, wherein, for calculating the virtual main point, the relative point data describe a first distance between a first one of the two actual auxiliary points and a first virtual auxiliary point symmetrical to the first actual auxiliary point with respect to the mid-sagittal plane as well as a second distance between a second one of the two actual auxiliary points and a second virtual auxiliary point symmetrical to the second actual auxiliary points with respect to the mid-sagittal plane.

* * * * *